United States Patent [19]

Ohya et al.

[11] Patent Number: 5,187,078
[45] Date of Patent: Feb. 16, 1993

[54] PLASMA-TYPE GLUTATHIONE PEROXIDASE GENE AND APPLICATION OF THE SAME

[75] Inventors: Masami Ohya, Tomakomai; Junzo Mizoguchi; Takashi Onozawa, both of Shizuoka, all of Japan

[73] Assignee: Toyo Jozo Co., Ltd., Sizuoka, Japan

[21] Appl. No.: 540,115

[22] Filed: Jun. 19, 1990

[30] Foreign Application Priority Data

Jun. 22, 1989 [JP]  Japan .................................. 1-159870

[51] Int. Cl.$^5$ .................... C12N 9/08; C12N 15/53; C12N 15/70; C12N 15/79
[52] U.S. Cl. .................................. 435/69.1; 435/192; 435/240.1; 435/252.3; 435/320.1; 536/23.2
[58] Field of Search .................... 435/69.1, 192, 320.1; 536/27

[56] References Cited

U.S. PATENT DOCUMENTS 5,089,408  2/1992  Akasaka .............................. 435/192

FOREIGN PATENT DOCUMENTS 8807541  10/1988  World Int. Prop. O. .

OTHER PUBLICATIONS

Suggs, S. V. et al. "Use of Synthetic Oigonucleotides as hybridization probes," *PNAS* 78(11):6613–6617 (1981).
Sukenaga, Y. et al. "CRNA sequence coding for human glutathione peroxidase," *Nucleic Acids Research*, 15:7178 (1987).
Journal of Biological Chemistry, vol. 262, No. 36, Dec. 25, 1987, pp. 17398–17403, Baltimore, US.
K. R. Maddipati et al.: "Characterization of the Major Hydroperoxide-reducing Activity of Human Plasma" *abstract, p. 17401, left-hand column, lines 18–28, p. 17402, right-hand column, lines 29–37*.
Archives of Biochemistry and Biophysics vol. 256, No. 2, Aug. 1, 1987, pp. 677–686, New York, US.
K. Takahashi et al.: "Purification and characterization of human plasma glutathione peroxidase: a selenoglycoprotein distinct from the known cellular enzyme".
Journal of Biochemistry vol. 108, No. 2, Aug. 1990, pp. 145–148, Tokyo, JP.
K. Takahashi et al.: "Primary structure of human plasma glutathione peroxidase deduced from cDNA sequences" *abstract; FIGS. 2,3*.
Febs Letters (Vol. 32, pp. 132–134, 1973).
The Embo Journal (Vol. 5, pp. 1221–1227, 1986).
The Journal of Biological Chemistry (Vol. 250 pp. 5144–5149, 1975).
Biochem. J. (Vol. 177, (pp. 471–476, 1979).
Chem. Pharm. Bull. (Vol. 131, (1), pp. 179–185, 1983).
Nucleic Acids Research (Vol. 15, pp. 10050–10051, 1987).
Nucleic Acids Research (Vol. 15, pp. 7178–7179, 1987).

*Primary Examiner*—Robert A. Wax
*Assistant Examiner*—Dian Cook
*Attorney, Agent, or Firm*—Young & Thompson

[57] ABSTRACT

DNA having genetic information of a human plasma-type glutathione peroxidase h-p·GSHPx was identified and disclosed. The enzyme, h-p·GSHPx, is produced by the expression of said DNA genetic information by a transformant holding a vector into which said DNA is incorporated. The DNA and the transformant ensures efficient production of human plasma type h-p·GSHPx. The enzyme exhibits lipid peroxide extinction activity, and is considered to be useful for the treatment or the cure or the prevention of these diseases.

11 Claims, 1 Drawing Sheet

PLASMA-TYPE GLUTATHIONE PEROXIDASE GENE AND APPLICATION OF THE SAME

BACKGROUND OF THE INVENTION

1. Field of the Invention

This invention relates to a DNA having genetic information of a human plasma-type glutathione peroxidase, a vector containing said DNA, a transformant holding said vector, a polypeptide produced by the expression of said DNA genetic information by the transformant.

2. Description of the Background

Glutathione peroxidase is an enzyme having glutathione as a substrate and catalyzing a reaction in which two moles of glutathione and one mole of hydrogen peroxide are converted into two moles of glutathione oxide and two moles of water. The enzyme is known to be present in tissues and organs of mammals, e.g. in liver, kidney, heart, lung, blood cells, plasma, and the like [Flohe et al., *FEBS Lett.*, 32, 132-134 (9173)], and to play an important role in the disposition of in-vivo peroxides by catalyzing 2-electron reduction of lipid peroxides produced by glutathione. Thus, glutathione peroxidase acts to extinguish in-vivo hydrogen peroxide and lipid peroxides. In particular, the activity of glutathione peroxidase to extinguish the lipid peroxide is of interest in relation to various diseases caused by lipid peroxides, which are known to impart a strong action to damage cell membranes. Burn (scald), for example, increases lipid peroxides in serum and causes damage to various organs, resulting in increase in such values as GOT, LDH, alkali phosphatase, and the like. Increase in the amount of lipid peroxides in serum which is also observed in patients suffering from diabetes mellitus causes damage to blood vessels, which are considered to be a cause of arteriosclerosis and cerebral apoplexy. Moreover, as a direct action, lipid peroxides denature LDH (low density lipoprotein) in serum. Intake of LDH thus produced by macropharge causes foam cells to be produced which are considered to be a cause of arterial sclerosis.

Based on the above observations, glutathione peroxidase, which exhibits the lipid peroxide extinction activity, is considered to be useful for the treatment or the cure or the prevention of these diseases.

Glutathione peroxidase is a protein containing selenium, which exists in the active site in the form of selenocystein (Sec). The opal codon TGA, which normally is a termination codon in a DNA sequence, codes for Sec in a cloned glutathione peroxidase gene derived from mouse [*EMBO Journal*, vol 5, No. 6, 1221-1227 (1986)].

Human glutathione peroxidases are isolated from blood cells [*J. Biol. Chem.*, 250, 5144-5149 (1975)], placenta [*Bioch. J.*, 177, 471-476 (1979)], or liver [*Chem. Pharm. Bull.*, 131, (1), 179-185 (1983)]0 as human blood cell-type glutathione peroxidase (hereinafter abbreviated as h-e.GSHPx). They are known to immunologically cross-over each other and to be composed of sub-units each having a molecular weight of about 20,600. The h-e.GSHPx was cloned from the cDNA library which was prepared from mRNA of kidney cells and liver cells, based on which the base sequence of their gene DNA have been determined [*Nuc. Acids Res.*, 15, 10051 (1987); *Nuc. Acids.*, 17, 7178 (1987)]. On the other hand, glutathione peroxidase was also confirmed to secrete in human plasma fractions. Sub-unit of this human plasma-type glutathione peroxidase (hereinafter abbreviated as h-p.GSHPx) were reported to exist as a homotetramer of glycoprotein having a molecular weight of 21,500-23,000 [*Archivs of Biochemistry and Biophysics*, 256, No. 2, 677-686 (1987); *J. Biol. Chem.*, 1,262, No. 36, 17398-17403 (1987)]. The h-e.GSHPx derived from blood cells and h-p.GSHPx derived from plasma do not immunologically crossover each other, and thus are considered to be different enzymes from the aspect of protein chemistry. Even though at least two types of glutathione peroxidases, h-e.GSHPx and h-p.GSHPx, have so far been confirmed to exist, the latter has never been cloned.

In order to utilize h-p.GSHPx as a medicine for curing diseases caused by activated oxygen or hydrogen peroxide a large amount of purified h-p.GSHPx sample is required. At the present, however, the production of a large amount of h-p.GSHPx in a purified form is difficult and undesirable from the aspect of the safety.

The present inventors have isolated h-p.GSHPx from human plasma fractions according to a known method [*Archivs of Biochemistry and Biophysics*, 256, No. 2, 677-686 (1987)], and digested this purified enzyme sample with trypsin to obtain four peptide fragments. Amino acid sequences of these peptide fragments determined according to the Edman degradation method were:

-? ? ? -Gly-Leu-Thr-Gly-Gln-Tyr-Ile-Glu-Leu-Asn-Ala-Leu-Gln-;

-Ala-Leu-Val-Ile-Leu-Gly-Phe-Pro-Cys-Asn-Gln-Phe-Gly-? ? ? -Gln-Glu-Pro-Asp-Glu-Asn-Ser-Glu-Ile-Leu-Pro-;

-Thr-Phe-Leu-Asp-Asn-Ser-Phe-Pro-; and

-Trp-Asn-Phe-Glu-? ? ? -Phe-Leu-Val-Gly-Pro-Asp-Gly-Ile-Pro-? ? ? -Met-Arg-, wherein ? ? ? denotes a site where the amino acid could not be identified.

Triplet codons for a 13 amino acid sequence which is a portion of the polypeptide amino acid sequences thus determined were estimated, from which a probe mixture of 39 anti-codon bases was prepared. This DNA probe was used to screen a cDNA library of λ-gt11 phage vector which was prepared from human placenta mRNA, thus identifying a gene consisting of 1,603 bases and encoding 225 amino acid residues. Analysis of the DNA sequence and the amino acid sequence proved that the selenocystein which is a site characteristic to glutathione peroxidase was encoded by an opal codon TGA, and the amino acid sequence in the neighborhood of the active center was -Ala-Ser-Tyr-*-Gly-Leu-Thr-, wherein * denotes a selenocystein residue. The amino acid sequence had a homology of only about 30% with that of h-e.GSHPx, and the homology of the base sequence with that of h-e.GSHPx was only about 25%. Furthermore, the h-p.GSHPx was found to have in its N-terminal side, an amino acid sequence of the formula -Ile-Ser-Gly-Thr-Ile-, and in its C-terminal side, an amino acid sequence of the formula -Leu-Gly-Thr-Ser-Asp-. This gene DNA was recombined into an expression vector and transformed, for example, in monkey kidney cells (COS) to express a homotetramer which comprises a sub-unit having a molecular weight of 23,000±2,000 and which could be discharged outside the cells by the action of the signal peptide which is characteristic to the amino acid sequence on the N-terminal side. The present inventors have thus prepared the h-p.GSHPx as well as its gene DNA, and have established a process for its preparation.

SUMMARY OF THE INVENTION

Accordingly, an object of this invention is to provide a DNA fragment comprising a base sequence coding for a polypeptide which is h-p.GSHPx, which polypeptide comprises, in a neighborhood of the polypeptide active center, amino acid sequence (I) of the formula -Ala-Ser-Tyr-*-Gly-Leu-Thr-, wherein * represents a selenocystein residue, in the N-terminal side of amino acid sequence (I), an amino acid sequence of the formula -Ile-Ser-Gly-Thr-Ile-, and in the C-terminal side of amino acid sequence (I), an amino acid sequence of the formula -Leu-Gly-Thr-Ser-Asp-; said h-p.GSHPx comprising a sub-unit having a molecular weight of 23,000±2,000, having glutathione as a substrate, and exhibiting glutathione peroxidase activity which catalyses a reaction converting two moles of glutathione and one mole of hydrogen peroxide into two moles of glutathione oxide and two moles of water.

Another object of the present invention is to provide a DNA vector which is capable of incorporating such a DNA fragment into microorganisms or animal cells.

Still another object of the present invention is to provide a transformant holding such a DNA fragment which is foreign with respect to the host organism and a polypeptide constituting such a h-p.GSHPx.

It is also an object of the present invention to provide a process for producing a polypeptide which comprises:

culturing a transformant holding said DNA fragment which is foreign with respect to the host organism in a medium containing selenium to express the genetic information of said DNA, and collecting the polypeptide from the culture broth.

Other objects, features and advantages of the invention will hereinafter become more readily apparent from the following description.

Figure 1:
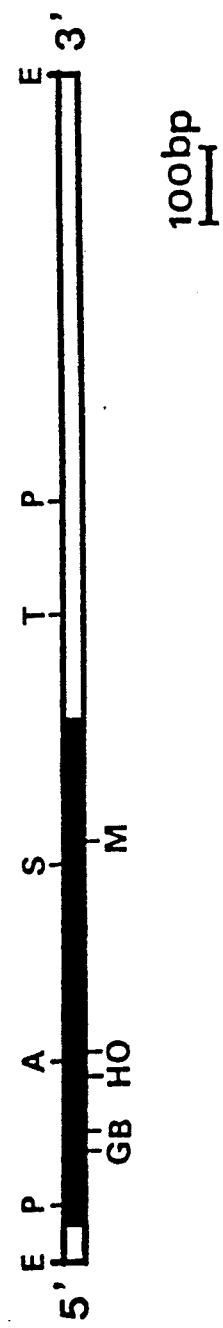
FIG. 1 shows a map showing restriction endonuclease sites of a DNA fragment containing the h-p.GSHPx gene, wherein cleavage sites by various restriction endonucleases are indicated by the following symbols.

P: Pst I
A: Aat I
S: Sac I
T: Eco T22I
E: Eco RI
B: Ban II
G: Bgl I
M: Mnl I
H: Hinc II
O: Eco O109I

DETAILED DESCRIPTION OF THE INVENTION
AND PREFERRED EMBODIMENTS

The h-p.GSHPx gene of the present invention may be prepared using a commercially available human placenta cDNA library or a library obtained by incorporating mRNA prepared from human placenta tissue into a vector. For example, a powdered human placenta tissue is homogenized with a guanidium solution to produce a suspension. The suspension is passed several times through a 18.5 gauge injection needle to fragment the high molecular DNA, multi-layered onto a 5.7 M cesium chloride solution, and centrifuged overnight at 25° C. and at 35,000 rpm. The precipitate is dissolved into water, treated with an equivalent amount of phenol-chloroform, followed by an addition of sodium acetate in an amount to make its concentration 0.3 M and by a further addition of 2.5-volume ethanol, thus effecting re-precipitation. The total RNA is then collected by centrifugation. The RNA is dissolved into water, heated for 5 minutes at 65° C. and quenched, following which a buffer containing SDS, EDTA, and NaCl is added. The mixture is charged into an oligo(dT)-cellulose column to elute only RNA possessing poly-A-tail. A first chain is synthesized from this poly-(A)+RNA using dNTPs (a mixture of equivalent amounts of dATP, dGTP, dCTP, and dTTP), oligo (dT), and a reverse transcriptase, then a second chain is prepared using RNaseH and DNA polymerase I. The Eco RI site existing within the gene is methylated with Eco RI methylase, the blunt ends are produced using $T_4$ DNA polymerase, and Eco RI linker is attached to the both ends, followed by the digestion with restriction endonuclease Eco RI and the size fractionation by electrophoresis to remove the surplus linker. The product is incorporated into phage vector λ-gt11, thus producing a cDNA library in which mRNA prepared from placenta tissue is incorporated into the λgt11 vector. This cDNA library can be used for preparing a library in which mRNA prepared from human placenta tissue is incorporated into the λgt11 vector. A probe consisting of several tens of bases may then be synthesized with reference to a known glutathione peroxidase. For simplicity, screening can be carried out using a synthesized oligonucleotide of a 39-base anti-codon corresponding to a peptide containing TGA coding for selenocystein (Sec) or its downstream peptide, e.g. -Gly-Leu-Thr-Gly-Gln-Tyr-Ile-Glu-Leu-Asn-Ala-Leu-Gln-. For the screening, a host microorganism, e.g. *Escherichia coli.* LE392, is infected with a library prepared from λgt11 vector and lyzed by the plaque hybridization method on an agar medium, and the phage is absorbed in a nylon membrane put onto the lyzed medium surface. The membrane is treated with alkali to denature the DNA. After neutralization, DNA is fixed by drying at 80° C. for 2 hours, the membrane is incubated at 37° C. for 4 hours in a pre-hybridization solution, e.g. a solution containing 5×SCC (1-fold; 150 mM NaCl, 15 mM sodium citrate), 5×Denhart solution, 50 mM sodium phosphate (pH 6.5), 0.1% SDS (sodium lauryl sulfate), 250 µg/ml non-homological DNA, e.g. salmon sperm DNA, and 20% formamide. To this solution the DNA probe of which the 5'-end of the DNA is labeled with $^{32}P$ as described above is added, followed by hybridization at 37° C. overnight. After this, the membrane is washed three times with 2×SSC, 0.1% SDS at room temperature, again washed with the same solution at 37° C. for 10 minutes, dried in the air, and subjected to autoradiograph to recover plaques existing at the place where signals appear. The plaque is again charged into the plate to purify it and to screen phage clones comprising the target h-p.GSHPx gene The purified phage thus screened is then used for the infection of the host organism, and the latter is cultured in a medium overnight. The culture broth is centrifuged to collect the supernatant. To the supernatant are added DNaseI and RNaseA, then the equivalent amount of 20% polyethylene glycol and 2.5 M NaCl, and the mixture is cooled, and centrifuged. The precipitate is suspended in SM (0.1 M NaCl/8 mM MgSO4/50mM Tris pH 7.5/0.01% gelatin solution). An equivalent amount of chloroform is added to the suspension, followed by centrifugation. Onto the mixture a water layer of which the density is adjusted to 1.6–1.4 by an addition of cesium chloride is layered and centrifuged. A band containing a phage having a density of 1.6–1.4 is collected, treated with protease, and the DNA is extracted with phenol. The extracted phage DNA is dissolved into a solution containing RNaseA and digested with restriction endonuclease Eco RI to obtain a fragment containing h-p.GSHPx gene of about 1.6 Kbp, which is then collected by gel electrophoresis. FIG. 1 shows a map showing the restriction endonuclease sites of this fragment containing the h-p.GSHPx gene of about 1.6 Kbp.

The fragment is then incorporated into the Eco RI site of plasmid pUC118, ligated, and subcloned, thus obtaining plasmid pUC118-p.GSHPx gene in which h-p.GSHPx gene is incorporated into the Eco RI site of plasmid pUC118. For the subcloning, instead of the pUC118, plasmids of which the host is microorganisms belonging to genus Escherichia and which have suitable restriction endonuclease sites such as pBR322, pBR325, pACYC184, pUC12, pUC18, pUC19, and the like can be used. Plasmids pUB110, pC194, and the like of which the host microorganisms are those belonging to genus can also be used. In order to confirm if the incorporated plasmid pUC118-p.GSHPx containing h-p.GSHPx gene expresses the target h-p.GSHPx activity, a suitable effective expression vector can be constructed. In the construction of such an expression vector, a plasmid suitable for the host microorganism *Escherichia coli* (e.g. *Escherichia coli* DH1, *Escherichia coli* HB101, *Escherichia coli* MV1184, *Escherichia coli* MV1304, *Escherichia coli* W3110, *Escherichia coli* C600), for example, plasmids pINI, pIN III, etc. can be used. When *Bacillus Subtilis* is used as a host microorganism, plasmids, pTUB218, pTUB285, and the like can be used. Alternatively, plasmids such as pAM82 and the like of which the host microorganism is a yeast such as *Saccharomyces cerevisiae* and the like may be used as an expression vector. Furthermore, a host can be animal cells such as monkey kidney cells (COS), Chinese hamster ovary (CHO) cells, or CHO-dhfr (dehydrofolate reductase) into which a virus vector which is a SV40 virus promoter capable of expressing a foreign DNA, e.g. plasmid pSVL (produced by Pharmasia), plasmid pSV2-dhfr (produced by BRL). In incorporating such a vector into the host organism, a plasmid vector prepared as mentioned above may be directly introduced into COS cells, CHO cells, or the like using calcium phosphate; or the competent cell method, the polyethylene glycol method, or the like which are conventionally known as methods of incorporating a plasmid into a host organism can be used to obtain a transformant. For incorporation into a host organism the vector may be suitably digested with restriction endonucleases according to a conventional method so as to delete or add sites which are appropriate to effect the ligation with the DNA fragment site containing h-p.GSHPx gene to be incorporated. For example, competent *Escherichia coli* MV1184 is transformed with plasmid pUC118-p.GSHPx and h-p.GSHPx gene is collected in the same manner as described above to confirm the DNA sequence. The transformant was named *Escherichia coli* MV-pUC118-p.GSHPx and deposited with Fermentation Research Institute, Agency of Industrial Science and Technology under the Budapest Treaty; deposition No. 2482, FERM BP-2482. The plasmid was named pUC118-p.GSHPx.

In constructing the expression vector, in order to confirm the expression of the target h-p.GSHPx and to effect the expression by COS cells or CHO cells, the plasmid pUC118.GSHPx containing h-p.GSHPx gene is digested by a restriction endonuclease to produce a DNA fragment containing h-p.GSHPx gene, which was inserted into the Sma I restriction endonuclease site of plasmid pSVL to obtain plasmid pSVL-p.GSHPx. This plasmid is then used for transforming competent *Escherichia coli* DH1 to produce transformed *Escherichia coli* DH1-pSVL-p.GSHPx. COS cells or CHO cells are also transformed with the plasmid pSVL-p.GSHPx. These transformed cells can be cultured in a medium containing serene according to a conventional tissue culture method, i.e., a method for culturing animal cells such as CHO cells. For example, the transformant is inoculated into a COS or CHO cell culture medium, such as, for example, into a Dulbecco's-modified Eagle's MEM medium containing 10% FCS and 0.01–0.05 μM selenious acid, in an incubator or, for simplicity, in a Shale, in an amount of about $10^4/cm^2$ and cultured at 30°–37° C. for 2–6 days. The supernatant of the culture broth is collected and subjected to the detection of the target h-p.GSHPx activity to confirm the expression of h-p.GSHPx. The enzyme, h-p.GSHPx, is then collected from the supernatant and purified by a suitable means which is conventionally applicable to enzyme recovery and purification. The solution containing h-p.GSHPx thus obtained is subjected to one or more of the means selected from vacuum concentration, concentration using membrane, desalting using ammonium sulfate, sodium sulfate, or the like, fractional precipitation using a hydrophilic solvent such as methanol, ethanol, acetone, or the like, and other suitable means, thus obtaining precipitate containing h-p.GSHPx. The precipitate is further purified, if required, for example, by dissolving it into water or a buffer solution and by dialyzing the solution to remove low molecular weight impurities, or further by ion exchange chromatography, adsorption chromatography, or gel filtration using absorbents or gel filtration agents. Purified h-p.GSHPx thus obtained may be stored after lyophilization.

The DNA of h-p.GSHPx which is the target product of the present invention has, for example, a base sequence represented by SEQ ID No. 1. shown later in this specification. This novel DNA has an opal codon TGA coding for selenocystein (Sec) and encodes a polypeptide consisting of 225 amino acid residues, and the amino acid sequence has in the neighborhood of its active center, amino acid sequence (I) of the formula -Ala-Ser-Tyr-*-Gly-Leu-Thr-, wherein * represents a selenocystein residue, in the N-terminal side of amino acid sequence (I), an amino acid sequence of the formula -Ile-Ser-Gly-Thr-Ile-, and in the C-terminal side of amino acid sequence (I), an amino acid sequence of the formula -Leu-Gly-Thr-Ser-Asp-. In this gene DNA, the 5,-end which is in the upstream of GCC (Ala) may have any codon so long as the same codes for an amino acid. In addition, the 5'-end side may have one or more codons encoding an amino acid, preferably ATG. It may further be recombined with a polydeoxyribonucleic acid corresponding to a suitable signal peptide. A codon in the 3'-end which is the downstream of AAG (Lys) may be a translational termination codon or any codon encoding an amino acid or a peptide. In addition, there can be one or more codons encoding an amino acid or a peptide at the 3'-end side, provided that in this instance it is desirable that a translational termination codon, e.g. TAA, be present at the 3'-end of these codons.

The polypeptide expressed by the novel DNA coding for an amino acid sequence of a polypeptide which constitutes a h-p.GSHPx is a homotetramer which comprises a sub-unit having a molecular weight of 23,000±2,000, and which immunologically crosses over known h-p.GSHPx. An example of the amino acid sequence of the polypeptide h-p.GSHPx determined from the base sequence is shown as SEQ ID No. 1. It is a 225-amino acid sequence having, in the neighborhood of its active center, an amino acid sequence (I) of the formula -Ala-Ser-Tyr-***-Gly-Leu-Thr-, corresponding to a base sequence of, for example, 5'-GCCAGC-TACTGAGGCCTGACG-3' (bases 208–228 when the base A of the initiating codon ATG is taken as base 1). It has in the N-terminal side of amino acid sequence (I), an amino acid sequence of the formula -Ile-Ser-Gly-Thr-Ile- which corresponds to a base sequence of, for example, 5'-ATAAGTGGCACCATT-3' (bases 106–120 when the base A of the initiating codon ATG is taken as base 1). It further has in the C-terminal side of amino acid sequence (I), an amino acid sequence of the formula -Leu-Gly-Thr-Ser-Asp- which corresponds to a base sequence of, for example, 5'-CTGGGTACATCTGAC-3' (bases 487–501 when the base A of the initiating codon ATG is taken as base 1).

In place of the above-mentioned COS cells microorganisms may be used as host organisms to obtain a transformant using a suitable expression vector. In order to obtain h-p.GSHPx using such a microorganism transformant, a microorganism belonging, for example, to *Escherichia coli*, can be transformed, and such a transformant microorganism is cultured for the expression of the target h-p.GSHPx. A liquid culture method can be employed. For industrial scale production, culture under deep aerobic stirring conditions is advantageous. A wide variety of nutrients conventionally used for bacterial culture can be used for culturing the microorganism. Specifically, any carbon compounds which are utilizable can be used as carbon sources. These include, for example, glucose, sucrose, molasses, glycerol, starch hydrolyzate, and the like. As nitrogen sources, any available nitrogen compounds can be employed, including corn steep liquor, soybean powder, casein hydrolyzates, peptones, meat extracts, yeast extracts, ammonium sulfate, ammonium chloride, and the like. Other ingredients, including water-soluble salts such as phosphates, chlorides, sulfates, carbonates, and nitrates, e.g. salts of sodium, potassium, calcium, magnesium, iron, zinc, copper, etc., may be added to the medium as appropriate. In addition selenious acid is added to the concentration of about 0.05–10 µM. The culture temperature can be varied in a range in which the bacteria can grow and produce h-p.GSHPx. A preferable temperature range is about 20° to 42° C. for microorganisms *Escherichia coli*. The culture time may be varied to some degree depending on the culture conditions. Basically, the culture is terminated at the time when the yield of h-p.GSHPx reaches maximum. In usual practice, this takes about 12 to 72 hours. After the culture, the culture broth containing h-p.GSHPx may be, as is, collected and purified. Since h-p.GSHPx is of plasma type, it can be secreted from the cells. In the case where the enzyme is present within cells, the culture broth is subjected to filtration, centrifugation, or the like to collect cells. The cells are destroyed either by mechanical means, e.g. by a ball mill, ultrasonic wave, or by enzymatic means using lysozyme or the like, and to the destroyed cells a chelating agent or a suitable surfactant is added, as required, to solubilize h-p.GSHPx, thus separating and collecting h-p.GSHPx, following which the enzyme is purified by one or more of the aforementioned separation and purification means.

The activity of h-p.GSHPx thus prepared is measured by mixing 0.1 ml of a h-p.GSHPx solution with 0.89 ml of a reaction solution containing 0.1 M Tris-hydrochloride (pH 8.0), 0.2 mM reducing-type NADP, 0.5 mM EDTA, 2 mM glutathione, and 1 unit of glutathione reductase, adding 10 µl of t-butylhydroperoxide (final concentration: 70 µM) to the mixture, followed by measurement of the absorbance at 340 nm to determine the decrease in the amount of the reducing-type NADP by oxidation. The activity of h-p.GSHPx was confirmed by this method, demonstrating that h-p.GSHPx was produced.

In the description of this specification, amino acids, peptides, nucleic acids, and nucleic acid-related compounds are abbreviated according to the prevailing standards. All designations of amino acids denote the L-isomers.

Other features of the invention will become apparent in the course of the following description of the exemplary embodiments which are given for illustration of the invention and are not intended to be limiting thereof

EXAMPLES

Example 1

20 g of human placenta was powdered in liquid nitrogen, and homogenized with 40 ml of 6 M guanidine isothiocyanate, and passed through a 18.5 guage injection needle to fragment the high molecular DNA and to decrease its viscosity. The homogenate was multi-layered onto ⅓-volume of a 5.7 M cesium chloride-0.1 M EDTA solution (pH 7.5) and centrifuged for 18 hours at 25° C. and at 35,000 rpm. The precipitate was dissolved into 3 ml of water, treated with an equivalent amount of phenol-chloroform. The water layer was transferred to another test tube, followed by an addition of 1/10 volume of 3 M sodium acetate and 2.5 volume of ethanol. After centrifugation, the residue was collected and dried in vacuo to produce 5 mg of crude RNA.

The precipitate was dissolved into 1.5 ml of water, incubated at 65° C. for 5 minutes and quenched, following which 1.5 ml of a buffer solution; 40 mM Tris-hydrochloride (pH 7.6), 1.0 M NaCl, 2 mM EDTA, and 0.2% SDS, was added. The whole mixture was absorbed into a column of 75 mg of oligo(dT)-cellulose (product of Pharmacia) which had been equilibrated with a buffer; 20 mM Tris-hydrochloride (pH 7.6), 0.5 M NaCl, 1 mM EDTA, and 0.1% SDS. After washing with 10 ml of the same buffer, 5 ml of a buffer; 20 mM Tris-hydrochloride (pH 7.6), 0.1 M NaCl, 1 mM EDTA, and 0.1% SDS, was passed through the column to elute RNAs other than poly(A)+RNA. Poly(A)+RNA was then eluted with a buffer; 10 mM Tris-hydrochloride (pH 7.5), 1 mM EDTA and 0.05% SDS. To 1 ml of a fraction initially discharged were added 1/10-volume 3 M sodium acetate and 2.5-volume ethanol, and the mixture was allowed to stand overnight at −20° C., centrifuged for 30 minutes at 15,000 rpm to collect the precipitate. The precipitate was dried in vacuo to obtain 50 µg of poly(A)+RNA.

Example 2

Poly(A)+RNA prepared in Example 1 was dissolved into water to the concentration of 1 μg/μl. 5 μl of the solution was transferred to a micro-tube, heated for 5 minutes at 65° C., and quenched. To the solution were added a buffer; 50 mM Tris-hydrochloride (pH 8.3), 10 mM MgCl$_2$, 140 mM KCl, 10 mM dithiothreitol, and 2 mM dNTPs (a mixture of equivalent amounts of dATP, dGTP, dCTP, and dTTP); 5 μg of oligo (dT) (product of Pharmacia); and 1.5 unit of a reverse transcriptase (Product of Takara Shuzo Co., Ltd.) to make the total volume to 20 μl, and the mixture was reacted for 1 hour at 42° C. To the reaction mixture were added a buffer; 80 mM Tris-hydrochloride (pH 7.5); 200 mM KCl, 10 mM MgCl$_2$, and 25 μg/ml BSA; 60 units of RNaseH (Product of Takara Shuzo Co., Ltd.); and 5 units of DNA polymerase I (product of Beringer Manheim) to make the total volume 150 μl. After reacting for 1 hour at 12° C. then for 1 hour at 22° C. and terminating the reaction by an addition of 20 μl of 0.25 M EDTA and 10 μl of 10% SDS, an equivalent amount of phenol-chloroform was added, followed by centrifuge at 10,000 rpm for 5 minutes. To the water layer was added an equivalent amount of 4 M ammonium acetate and 2-fold volume of ethanol, and the mixture was again centrifuged at 15,000 rpm for 15 minutes to collect the residue. The residue was collected and dried in vacuo, and to this a buffer; 100 mM Tris-hydrochloride (pH 8.0), 10 mM EDTA, 80 μM S-adenosylmethionine, 100 μg/ml BSA; and 2 units of Eco RI methylase (Promegabiotec Co.) were added to make the total volume 10 μl, and the mixture was reacted at 37° C. for 1 hour. To the resulting reaction mixture were added 40 μl of water, an equivalent amount of phenol-chloroform, and the mixture was centrifuged to separate a water layer. After an addition of an equivalent amount of 4 M ammonium acetate and 2-fold volume of ethanol, the mixture was allowed to stand for 15 minutes at −70° C., centifuged at 15,000 rpm for 15 minutes to collect the residue. To the residue were added a buffer; 67 mM Tris-hydrochloride (pH 8.8), 6.7 mM MgCl$_2$, 16.6 mM ammonium sulfate, 10 mM 2-mercaptoethanol, 6.7 μM EDTA, 0.167% BSA; dATP, dGTP, dCTP, and dTTP, each at 750 μM; and 4 units of T4 DNA polymerase (manufacture by Takara Shuzo Co., Ltd.), to make the total volume 12 μl, following which the mixture was reacted at 37° C. for 1 hour. The resultant mixture was treated with an equivalent amount of phenol-chloroform and ethanol to produce precipitate. The precipitate collected by centrifugation was dried in vacuo and to this were added 1 μl of Eco RI linker, a buffer solution; 50 mM Tris-hydrochloride (pH 7.6), 10 mM MgCl$_2$, 10 mM dithiothreitol, 0.1 mM spermidine, 0.1 mM EDTA, 1 mM ATP, and 3 units of T4 polynucleotidekinese (manufacture by Takara Shuzo Co., Ltd.), to make the total volume 10 μl, followed by a reaction at 37° C. for 30 minutes. The whole mixture was added to a sample which had been treated with T4 DNA polymerase. After an addition of 60 units of T4 ligase (product of Pharmacia) and reacting the mixture at 14° C. overnight, a solution of 100 mM NaCl, 50 mM Trishydrochloride (pH 7.5), 10 mM MgCl$_2$, 7 mM 2-mercaptoethanol, 100 μg/ml BSA, and 250 units of Eco RI was added to the resulting reaction mixture to make the total volume 40 μl, followed by a further reaction at 37° C. for 2 hours. The reaction mixture thus obtained was fractionated in 1% low melting point agarose gel to collect a 600–2,000 base DNA-containing gel. The gel was incubated at 65° C. for 10 minutes to melt and, after an addition of an equivalent amount of phenol and ice-cooling for 10 minutes, the mixture was centrifuged at 4° C. for 10 minutes at 15,000 rpm. To the water layer thus obtained was added an equivalent amount of phenol and the same procedure was repeated. The water layer was treated twice with chloroform and 1/10 volume of 3 M sodium acetate and 2.5-fold volume of ethanol were added. After having been allowed to stand for 15 minutes at −70° C., the mixture was centifuged at 15,000 rpm for 15 minutes to collect the residue. The residue was washed twice with 75% ethanol, dried in vacuo, and, after an addition of 1 μg of phage vector, λgt11 (manufactured by Stratgene Corp.), reacted a 26° C. for 10 minutes using a ligation kit (product of Takara Shuzo Co., Ltd.). After this, the sample was reacted using an in vitro packaging kit (manufactured by Stratgene Corp.). *Escherichia coli* LE392 (product of Stratgene Corp.) was infected with the τ phage. The total number of the phage was counted to be $5.0 \times 10^5$ pfu (plaque forming unit).

Example 3

The human placenta cDNA library ($5.0 \times 10^5$ pfu) thus prepared was distributed on 1.5% LB agar medium (containing 10 g of bacto-trypton, 5 g of bacto-yeast extract, and 10 g of NaCl for 1 liter) using *Escherichia coli* LE392 to select the clone of h-p.GSHPx gene using the plaque hybridization method.

Furthermore, based on the result of the trypsin hydrolysis of human plasma-type GSHPx which was purified according to a known method [*Archivs of Biochemistry and Biophysics*, 256, No. 2, 677–686 (1987)], a 39 base anticodon oligonucleotide: 5'-T/C TGIAGIGC A/G TTIAG T/C TCIAT A/G TA T/C TGICCIG-TIAGICC-3', wherein I stands for inosinic acid, which corresponds to -Gly-Leu-Thr-Gly-Gln-Tyr-Ile- Glu-Leu-Asn-Ala-Leu-Gln-, was synthesized.

The plaque lysed on a LB plate was transferred onto a nylon membrane, and the membrane was treated with 0.5 M NaOH-1.5 M NaCl for 5 minutes, then with 3 M sodium acetate (pH 5.5) for 5 minutes, and dried at 80° C. for 2 hours under a reduced pressure. The membrane was put into a vinyl pack, and incubated at 37° C. for 4 hours in 10 ml of a solution of 5-fold SSC (1-fold; 150 mM NaCl, 15 mM sodium citrate), 5-fold Denhart solution (1-fold 0.02% phycol, 0.02% polyvinyl pyrrolidone, 0.02% BSA), 50 mM sodium phosphate (pH 6.5), and 0.1% SDS (sodium lauryl sulfate), 250 μg/ml salmon sperm DNA, and 20% formamide. After removing the liquid, 20 ng of the aforementioned synthesized oligonucleotide probe ($10^8$ cpm/μg) of which the 5'-end was labeled with $^{32}$P was added and the hybridization was carried out at 37° C. overnight. After this, the membrane was washed three times with 2×SSC, 0.1% SDS at room temperature, again washed with the same solution at 37° C. for 10 minutes, dried in the air, and subjected to autoradiograph overnight. Portions of the medium at which signals appeared was cut out and suspended into 1 ml of a SM solution (0.1 M NaCl, 8 mM MgSO$_4$, 50 mM Tris-hydochloride (pH 7.5), 0.01% gelatin). The suspension was diluted, charged onto a LB plate for the formation of λ phage plaques and the screening was repeated using the same probe. Plaque were purified to obtain two stocks of the clone.

Example 4

A host microorganism, *Escherichia coli* LE392, was infected with the recombinant λ-phage 1×10⁵ pfu prepared in Example 3 and distributed onto two sheets of LB agar medium plate (13 cm×9 cm). 15 ml of SM solution was added to each sheet to infiltrate pharge thereinto. The infiltrate together with the upper agar layer was transferred to a test tube and centrifuged at 8,000 rpm for 10 minutes. To the supernatant were added 60 units of DNaseI (product of Takara Shuzo Co., Ltd.) and 100 μg of RNaseA (product of Sigma Co.), and the mixture was incubated at 37° C. for 30 minutes. After an addition of an equivalent amount of 20% polyethylene glycol and 2.5 M NaCl, the mixture was ice-cooled for 1 hour, centrifuged at 15,000 rpm for 20 minutes to obtain a residue. The suspension of the residue in 0.5 ml of SM solution was treated with an equivalent amount of chloroform and centrifuged to separate a water layer. Cesium chloride was added to the water layer to make the density of the solution 1.15. This solution was layered onto SM solutions to which cesium chloride was added to make their densities 1.6 (2 ml), 1.5 (3 ml), and 1.4 (3 ml), and centrifuged at 30,000 rpm for 3 hours. A band appeared between densities 1.4 and 1.5 which contained the phage was taken out and dissolved into Tris-hydrochloride (pH 7.5), centrifuged at 40,000 rpm for 1 hour to obtain a residue. The residue was treated with a solution of 20 mM EDTA, 0.5% SDS, 50 μl/mg protease K (product of Sigma Co.) at 65° C. for 1 hour. After an addition of an equivalent amount of phenol to the reaction solution, followed by centrifugation to separate a water layer, this water layer was again treated with an equivalent amount of phenol-chloroform and again centrifuged. The water layer obtained was treated with chloroform, and 1/10 volume of 3 M sodium acetate and 2.5 volume of ethanol were added to it. After having been allowed for 15 minutes at −70° C., the mixture was centrifuged at 15,000 rpm for 15 minutes to collect a residue, which was washed twice with 75% ethanol and dried under reduced pressure. The residue was dissolved into 50 μl of water containing 5 μg/ml of RNaseA. 10 μl of an aliquot of the solution was completely digested with Eco RI (product of Toyo Boseki Co., Ltd.) in H buffer [Maniatis et al., *Molecular Cloning* 104, Cold Spring Harbor (1982)], thus obtaining h-p.GSHPx clone of which fragment had the maximum length of 1.6 kbp. The fragment of the length of 1.6 kbp obtained by the digestion with Eco RI was recovered by low melting point agarose gel electrophoresis. This fragment of about 1.6 kbp length was digested by various restriction endonucleases to develop a restriction endonuclease map as shown in FIG. 1, wherein cleavage sites by various restriction endonucleases are indicated by the following symbols:

P: Pst I
A: Aat I
S: Sac I
T: Eco T22I
E: Eco RI
B: Ban II
G: Bgl I
M: Mnl I
H: Hinc II
O: Eco O109I The several cleavage sites detected other than those shown in FIG. 1 for restriction endonucleases G, B, O, and M are omitted.

Furthermore, after complete digestion of vector pUC118 with Eco RI, 0.5 unit of bacteria alkaliphosphatase (product of Toyo Boseki Co., Ltd.) was added and reacted in 50 mM Tris-hydrochloride (pH 8.0) at 65° C. for 1 hour (such a reaction is hereinafter called "BAP treatment"). The reaction product was treated twice with phenol-chloroform solution. To the water layer were added 1/10 volume of 3 M sodium acetate and 2 volume of ethanol, and the mixture was centrifuged to collect the vector. Insertion fragment recovered from the gel and the vector pUC118 digested with Eco RI were joined using a ligation kit (product of Takara Shuzo Co., Ltd.) to obtain plasmid, which was named pUC118-p.GSHPx.

*Escherichia coli* MV1184 (purchased from Takara Shuzo Co., Lt.) cultured in 100 ml ψ medium (pH 7.6; containing 20 g of bacto-trypton, 5 g of bacto-yeast extract, and 14 g of MgSO₄ for 1 liter) in a logarithmic growth phase was collected and suspended in 40 ml of ice-cooled solution of 30 mM potassium acetate, 100 mM RbCl, 10 mM CaCl₂, 50 mM MnCl₂, and 15% glycerol (pH 5.8). After having been for 15 minutes at 0° C., cells were collected by centrifugation, and again suspended into 4 ml of a 10 mM MOPS buffer solution (product of Dotai Co.), 75 mM CaCl₂, 10 mM RbCl, and 15% glycerol (pH 6.5), following which the suspension was allowed to stand at 0° C. for 15 minutes to produce competent cells.

To 200 μl of the *Escherichia coli* suspension 20 μl of the above solution of plasmid pUC118-p.GSHPx DNA which had been ligated was added and the mixture was incubated at 0° C. for 30 minutes, heat-treated for 90 seconds at 42° C. After an addition of 800 μl of LB medium, it was incubated at 37° C. for 60 minutes. The product was inoculated into LB agar medium containing 50 μg/ml ampicillin, 0.02% X-gal (5-bromo-4-chloro-3-indolyl-β-galactoside), and 50 μM IPTG (isopropyl-β-D-thio-glactopyranoside), and incubated at 37° C. overnight to obtain transformants. A single white colony of the transformant was cultured overnight in 2 ml of LB medium containing 50 μg/ml ampicillin, and the cells were collected by centrifuge. The cell was named *Escherichia coli* MV-pUC118-p.GSHPx (Deposition No. FERM BP-2482).

To the collected cells were added 0.6 ml of 50 mM Tris-hydrochloride buffer (pH 8.0), 50 mM EDTA (pH 8.0), 15% sucrose containing 1 mg/ml lysozyme (product of Sigma Co.). The mixture was reacted at 37° C. for 15 minutes, mixed with 12 μl of 10% SDS. To this was added 60 μl of 5 M potassium acetate. The mixture was allowed to stand at 0° C. for 30 minutes and centrifuged at 15,000 rpm for 10 minutes. The supernatant obtained was treated with an equivalent amount of phenol-chloroform, and the water layer was washed twice with ether. After an addition of 2 volume of ethanol, the mixture was allowed to stand at −70° C. for 15 minutes, centrifuged at 15,000 rpm for 15 minutes to collect a residue. The residue was washed twice with 75% ethanol, dried under reduced pressure, dissolved in an aqueous solution of 5 μg/ml RNaseA, thus digesting with Eco RI and selecting clone which contained insertion fragment.

Example 5

A single colony containing the above clone was cultured at 37° C. overnight in 6 ml of LB medium containing 50 μg/ml ampicillin. 5 μl of the cells were transferred to 500 ml of LB liquid and cultured at 37° C. To the culture broth at logarithmic growth phase, 20 μg/ml of chloramphenicol was added and the mixture was further cultured overnight. The culture broth was centrifuged at 6,000 rpm for 10 minutes to collect cells. To the cells were added 15 ml of 8% sucrose, 10% Triton X, 25 mM EDTA, 50 mM Tris-hydrochloride buffer (pH 8.0) and 1.5 ml of 10 mg/ml lysozyme dissolved in 0.25 mM Tris-hydrochloride buffer (pH 8.0) to lyse the cells with heating. The supernatant obtained by centrifuge at 14,000 rpm for 30 minutes was treated with an equivalent amount of phenol-chloroform. To the water layer thus obtained were added 1/10 volume of 3 M sodium acetate and 2 volume of ethanol, and the mixture was allowed to stand for 15 minutes at −70° C., centrifuged at 3000 rpm for 15 minutes to collect a residue, which was dissolved into 21 ml of Tris-hydrochloride buffer (pH 7.4). 20 g of cesium chloride and 1 ml of 10 mg/ml ethidium bromide were added and the mixture was centrifuged at 50,000 rpm overnight at 4° C. Closed plasmid DNA was separated from the residue. An equivalent amount of butanol was added and the mixture was centrifuged to remove the residual ethidium bromide. The water layer was treated twice with butanol, and filtered with CL4B Sephallose gel (product of Pharmacia) which had been washed twice with a Tris-hydrochloride buffer (pH 7.4) containing 0.2 M NaCl to remove the impurities. Two (2) volume of ethanol was added to the filtrate, and the mixture was allowed to stand for 15 minutes at −70° C., centrifuged at 3,000 rpm for 30 minutes to collect a residue, which was washed twice with 75% ethanol, dried, and adjusted to a concentration of 1 μg/μl. In order to determine the base sequence of the plasmid throughout its total length, the DNA was digested with restriction endonucleases Eco RI/Sac I (plasmid pUC118, Eco RI/Sac I), Eco RI/Pst I (plasmid pUC118, Eco RI/Pst I), Eco RI/Aat I (plasmid pUC119, Sma I), Aat I/Sac I (plasmid pUC119, Sma I), Sac I/Eco T22I (plasmid pUC119, Sma I), were joined with each plasmid pUC vector and *Escherichia coli* MV1184, host microorganism, was transformed according to a conventional method. A single clone with which the insertion was confirmed was transferred to 10 ml of 2-fold YT medium (containing 16 g of bacto-trypton, 10 g of bacto-yeast extract, and 5 g of NaCl for 1 liter) containing 50 μg/ml ampicillin and 0.01% thiamine, cultured at 37° C. for 1 hour, followed by infection with 6×10⁸ pfu of helper phage M13KO7 (product of Takara Shuzo Co., Ltd.). After culturing overnight, the culture broth was centrifuged at 10,000 rpm for 10 minutes. 1/5 volume PEG-NaCl solution (20% polyethylene glycol 6000, 2.5 M NaCl) was added to the supernatant and the mixture was allowed to stand for 15 minutes. To the residue obtained by centrifuge at 15,000 rpm for 10 minutes was added water containing 5 μg/ml RNaseA for dissolution. After having been allowed to stand for 15 minutes, the solution was treated with an equivalent amount of phenol, and centrifuged. The water layer was treated with phenol-chloroform, and 1/10 volume of 3 M sodium acetate and a 2 volume of ethanol was added to it. The mixture was allowed to stand for 15 minutes at −70° C., centrifuged at 15,000 rpm for 15 minutes to collect a residue, which was washed twice with 75% ethanol and dried under reduced pressure. The base sequence of the single strand DNA thus prepared was determined by labeling 1 μg of the DNA using M13 sequence kit (product of Takara Shuzo Co., Ltd.).

Based on the above base sequence determination, it was found that the DNA fragment contained a base sequence encoding a polypeptide h-p.GSHPx. It consisted of 1603 bases encoding 225 amino acid residues, starting from the initiation codon ATG coding for Met (A is taken as base 1), containing a base sequence 5'-ATGGCCCGGCTGCTGCAG-3' encoding R-Ala-Arg-Leu-Leu-Gln- (wherein R stands for the initiation codon Met, or may be a hydrogen or other amino acid), Sec encoded by opal codon TGA at 217–219, a termination codon TAA at 679–681, and a base sequence 5'-GGGGTCAAGAGGAAGTAA-3' (wherein TAA stands for the termination codon, or may be a sequence encoding an amino acid sequence), encoding -Gly-Val-Lys-Arg-Lys. This base sequence is shown as SEQ ID No. 1. The h-p.GSHPx gene had a base sequence, in the neighborhood of its active center, coding for an amino acid sequence -Ala-Ser-Tyr-\*\*\*-Gly-Leu-Thr-, wherein \*\*\* represents a Sec residue).

The amino acid sequence, -Ala-Ser-Tyr-\*\*\*-Gly-Leu-Thr-, wherein \*\*\* denotes a selenocystein residue, existing in the neighborhood of the active center of h-p.GSHPx gene encoded by the base sequence 5'-GCCAGCTACTGAGGCCTGACG-3' (bases 208–228 when the base A of the initiating codon ATG is taken as base 1) was confirmed by the digestion with restriction endonucleases Hinc II and Eco RI of said DNA gene, which produced a DNA fragment of 202–228 bases of the sequence 5'-AACGTGGCCAGC-TACTGAGGCCTGACG-3', in which the codon frame starts from the first base A, which correspond to the amino acid sequence, -Asn-Val-Ala-Ser-Tyr-Sec-Gly-Leu-Thr-. In the same way, the amino acid sequence Ile-Ser-Gly-Thr-Ile, which is in the N-terminal side of said amino acid sequence in the neighborhood of the active center of h-p.GSHPx gene encoded by the base sequence 5'-ATAAGTGGCACCATT-3' (bases 106–120 when the base A of the initiating codon ATG is taken as base 1) was confirmed by the digestion with restriction endonucleases Bgl I and Ban II of said DNA gene, which produced a DNA fragment of 102–131 bases of the sequence 5'-TGGCATAAGTGGCAC-CATTTACGAGTACGG-3', in which the codon frame starts with second base G, which corresponds to an amino acid sequence of -Gly-Ile-Ser-Gly-Thr-Ile-Tyr-Glu-Tyr-Gly-. Furthermore, the amino acid sequence -Leu-Gly-Thr-Ser-Asp-, which is in the C-terminal side of said amino acid sequence in the neighborhood of the active center of h-p.GSHPx gene encoded by the base sequence 5'-CTGGGTACATCTGAC-3' (bases 487–501 when the base A of the initiating codon ATG is taken as base 1) was confirmed by the digestion with restriction endonucleases Sac I and Mnl I of said DNA gene, which produced a DNA fragment of 485–514 bases of the sequence 5'-TCCTGGGTACATCTGACCGCCTCTTCTGGG-3', in which the codon frame starts with the third base C, which corresponds to an amino acid sequence of -Leu-Gly-Thr-Ser-Asp-Arg-Leu-Phe-Trp-.

Example 6

A vector was constructed from animal cells in order to confirm the expression of the target h-p.GSHPx activity by plasmid pUC118-p.GSHPx into which the above h-p.GSHPx gene was inserted.

10 μg of plasmid pUC118-p.GSHPx DNA was digested with 15 units Eco RI in the aforementioned H buffer at 37° C. for 2 hours. The reaction liquid was treated with chloroformphenol, washed with ethanol, and to the DNA were added 50 mM Tris-hydrochloride buffer (pH 7.2), containing dATP, dGTP, dCTP, and dTTP, each at 5 mM, 10 mM MgSO$_4$, 0.1 mM dithiothreitol, 50 μg/ml BSA, and 10 units of Klenour fragment (product of Toyo Boseki Co., Ltd.). After the reaction for 1 hour at room temperature, the reaction mixture was subjected to 1% low melting point agarose gel electrophoresis to extract and purify a DNA fragment having about 1,600 base pairs. The DNA fragment was dried.

Separately, 3 μg of plasmid pSVL (product of Pharmacia) DNA was reacted for 2 hours at 30° C. in Sma I buffer [10 mM Tris-hydrochloride (pH 7.5), 7 mM MgCl$_2$, 20 mM KCl, 7 mM 2-mercaptoethanol, 100 μg/ml BSA] to which 8 units of Sma I (product of Toyo Boseki Co., Ltd.) was added and subjected to BAP treatment (hereinbefore defined), following which the DNA was joined with the DNA fragment having about 1,600 base pairs, of which the ends was made blunt, using the above-mentioned ligation kit. The product was added to 200 μl of competent *Escherichia coli* DH1 (ATCC 3849 provided by National Gene Research) which had been treated in the same way as the above-mentioned *Escherichia coli* MV1184 competent cells, allowed to stand at 0° C. for 30 minutes, then at 42° C. for 90 seconds, followed by an addition of 800 μl of LB medium and incubation at 37° C. for 1 hour. 300 μl of the product was inoculated into LB agar medium containing 50 μg/ml ampicillin, and cultured overnight to produce transformants. This transformant holding human GSHPx was named *Escherichia coli* DH1-pSVL-p.GSHPx and the plasmid held therein was named plasmid pSVL-p.GSHPx.

Example 7

Expression of h-p.GSHPx by COS cells was confirmed.

To 175 μl of a buffer (TBS) containing 25 mM Tris-hydrochloride (pH 7.4), 137 mM NaCl, 5 mM KCl, 0.7 mM CaCl$_2$, 0.5 mM MgCl$_2$, and 0.6 mM Na$_2$HPO$_4$, were added 4 mg of DEAE-dextran (product of Pharmacia) and 10 μg of the above-mentioned plasmid pSVL-p.GSHPx DNA. The mixture was added to COS cells (1×10$^8$) which had been cultured in D-MEM medium (product of Gibco Co.) containing 10% FCS and 10 nM selenious acid. The cells were then cultured using the same culture medium at 5% CO$_2$ concentration at 37° C. for 72 hours. The supernatant (0.1 ml) of the culture broth was mixed with 0.89 ml of a reaction solution containing 0.1 M Tris-hydrochloride (pH 8.0), 0.2 M reducing-type NADP, 0.5 mM EDTA, 2 mM reduced-type glutathione, and 1 unit of glutathione reductase (product of Sigma Co.), and to this 10 μl of t-butylhydroperoxide (final concentration: 70μM) was added. The absorbance at 340 nm was measured to determine the decrease in the amount of the reducing-type NADP by oxidation. As a result, the activity of h-p.GSHPx was found to be 0.01 unit when the activity of converting 1 μmol of reducing-type glutathione into oxidation-type at 37° C. for 1 minute was taken as 1 unit.

Furthermore, to the supernatant obtained from the above culture broth by centrifuge at 10,000 rpm for 15 minutes was added ammonium sulfate, and portions that precipitated between 25 to 50% was centrifuged at 15,000 rpm for 30 minutes to collect ammonium sulfate precipitate. This precipitate was dissolved into 10 ml of 10 mM phosphate buffer (pH 7.2) containing 0.7 mM mercaptoethanol, and dialyzed three times against 50-volume of the same buffer. Dialysing internal liquid was absorbed in DEAE-cellulose DE52 (3×10 cm columns; product of Wattman Corp.) and linear gradiently eluted with the same buffer at 0.1–0.5 M NaCl concentration. The active fraction eluted between 0.25–0.35 M NaCl concentration was absorbed by Bio-Gel HTP (2–7 cm; product of Biorad Corp.) and eluted with 20–200 mM potassium phosphate buffer (pH 7.2) containing 0.7 mM mercaptoethanol. The enzyme active fraction was further concentrated and subjected to molecular sieve using Sephadex G-200 (3×60 cm; product of Pharmacia) to obtain an enzyme active fraction. This fraction was again absorbed by DEAE Sephadex A25 (2×4 cm; product of Pharmacia), and linear gradiently eluted at 0–0.2 M NaCl concentration to obtain an enzyme fraction. The molecular weight measured on this fraction by Sephadex G-200 was found to be 100,000 daltons. SDS-polyacrylamide electrophresis resulted in a single band of the molecular weight of 23,000±2,000 dalton. The enzyme exhibited an immunological cross-over reaction against the antibody produced in following Reference Example 1.

Reference Example 1

(1) Extraction and purification of h-p.GSHPx from a human plasma fraction according to a known method [*Archivs of Biochemistry and Biophysics*, 256, No. 2, 677–686 (1987)]

To 1.8 l of human serum was added 1.2 l of saturated ammonium sulfate to make the ultimate concentration of ammonium sulfate 40%. The mixture was centrifuged at 10,000×g for 20 minutes, and the precipitate obtained was dissolved in a minimum amount of 20 mM sodium phosphate buffer (pH 7.2). The solution was dialyzed first against 100 volume of the same buffer, and then against 100 volume buffer 20 mM sodium phosphate buffer (pH 7.2) containing 0.7 mM 2-mercaptoethanol (such a buffer is hereinafter called Buffer A) to which 0.1 M NaCl was added. The dialyzing internal liquid was absorbed in DEAE-cellulose DE52 (3×10 cm columns; product of Wattman Corp.) which had been equilibrated with Buffer A, and linear gradiently eluted with the same buffer at 0.1–0.5 M NaCl concentration. The active fraction eluted between 0.25–0.35 M NaCl concentration was absorbed by Bio-Gel HTP (2×7 cm; product of Biorad Corp.) and eluted with 20–200 mM potassium phosphate buffer (pH 7.2) containing 0.7 mM mercaptoethanol. The enzyme active fraction was further concentrated and subjected to molecular sieve using Sephadex G-200 (3×60 cm; product of Pharmacia) to obtain an enzyme active fraction. This fraction was again absorbed by DEAE Sephadex A25 (2–4 cm; product of Pharmacia), and linear gradiently eluted at 0–0.2 M NaCl concentration to obtain an enzyme fraction. The molecular weight measured on this fraction by Sephadex G-200 was found to be about 100,000 dalton. SDS-polyacrylamide electrophoresis [the Lamery method: *Nature*, 227, 680–685 (1970)] resulted in a single band of the molecular weight of 23,000±2,000 dalton. The total amount of this sample product measured by protein quantitative analysis [the Lory method: *J. Biol. Chem.*, 193, 263–275 (1951)] was 320 μg.

(2) Determination of amino acid sequence

200 μg of the sample prepared in (1) was dissolved into 4 ml of 8 M urea containing 0.2% EDTA which was adjusted to pH 8.5 with 0.1% methylamine, and 0.1 ml of 2-mercaptoethanol was added to the solution. After allowing the mixture to stand for 4 hours, 270 mg of monoiodo acetate dissolved in 1 ml of 1 N NaOH was gradually added. The mixture was added to Sephadex G-25 (3.7×40 cm; product of Pharmacia) which had been equilibrated with 0.2 N acetic acid to obtain alkylated reduced protein. The product was dissolved into 1 ml of 2 M urea solution and digested with 1/50 weight trypsin (product of Funakoshi Co.) for 16 hours. The digested material was absorbed in TSK ODS-120T (product of Toyo Soda Co., Ltd.) and linear gradiently fractionated with acetonitrile at concentrations of 5–45%. Four (4) major peaks obtained was analyzed by PSG-1 autosequenser (product of Shimazu Manufacturing Co., Ltd.). These fragments had the following amino acid sequences in which ??? shows a portion at which amino acid could not be identified, ? ? ? -Gly-Leu-Thr-Gly-Gln-Tyr-Ile-Glu-Leu-Asn-Ala-Leu-Gln-;
-Ala-Leu-Val-Ile-Leu-Gly-Phe-Pro-Cys-Asn-Gln-Phe-Gly-? ? ? -Gln-Glu-Pro-Asp-Glu-Asn-Ser-Glu-Ile-Leu-Pro-;
-Thr-Phe-Leu-Asp-Asn-Ser-Phe-Pro-; and
-Trp-Asn-Phe-Glu-? ? ? -Phe-Leu-Val-Gly-Pro-Asp-Gly-Ile-Pro-???-Met-Arg-.

The DNA and the transformant of the present invention ensured the efficient production of human plasma type h-p.GSHPx. The present invention also isolated and identified an amino acid sequence of novel h-p.GSHPx derived from human being. Furthermore, the present invention clarified h-p.GSHPx gene, which has made it possible to supply h-p.GSHPx in a purified form.

Obviously, numerous modifications and variations of the present invention are possible in light of the above teachings. It is therefore to be understood that within the scope of the appended claims, the invention may be practiced otherwise than as specifically described herein.

SEQUENCE LISTING

1. SEQ ID No. 1
2. Length of the sequence: 681 base pairs (encodes a protein or peptide of 226 amino acid residues, containing Met which acts as an initiation codon.
3. Type of sequence:
   (1) Strandedness: double-stranded
   (2) Topology of the sequence: Linear
   (3) Type of molecular sequenced: cDNA to mRNA.
   (4) Original source: cDNA library derived from human placenta
   (5) Name: Glutathione peroxidase gene
   (6) Other information:
       Product: Glutathione peroxidase
       Subunit structure: 4 units
       Enzyme Committee No. 1.11.1.9
4. Sequence

```
ATG GCC CGG CTG CTG CAG GCG TCC TGC CTG CTT TCC CTG CTC CTG GCC
GGC TTC GTC TCG CAG AGC CGG GGA CAA GAG AAG TCG AAG ATG GAC TGC
CAT GGT GGC ATA AGT GGC ACC ATT TAC GAG TAC GGA GCC CTC ACC ATT
GAT GGG GAG GAG TAC ATC CCC TTC AAG CAG TAT GCT GGC AAA TAC GTC
CTC TTT GTC AAC GTG GCC AGC TAC TGA GGC CTG ACG GGC CAG TAC ATT
GAA CTG AAT GCA CTA CAG GAA GAG CTT GCA CCA TTC GGT CTG GTC ATT
CTG GGC TTT CCC TGC AAC CAA TTT GGA AAA CAG GAA CCA GGA GAG AAC
TCA GAG ATC CTT CCT ACC CTC AAG TAT GTC CGA CCA GGT GGA GGC TTT
GTC CCT AAT TTC CAG CTC TTT GAG AAA GGG GAT GTC AAT GGA GAG AAA
GAG CAG AAA TTC TAC ACT TTC CTA AAG AAC TCC TGT CCT CCC ACC TCG
GAG CTC CTG GGT ACA TCT GAC CGC CTC TTC TGG GAA CCC ATG AAG GTT
CAC GAC ATC CGC TGG AAC TTT GAG AAG TTC CTG GTG GGG CCA GAT GGT
ATA CCC ATC ATG CGC TGG CAC CAC CGG ACC ACG GTC AGC AAC GTC AAG
ATG GAC ATC CTG TCC TAC ATG AGG CGG CAG GCA GCC CTG GGG GTC AAG
AGG AAG TAA
```

What is claimed is:

1. An isolated DNA fragment consisting essentially of the base sequence represented by SEQ ID No. 1.
2. A DNA vector containing the DNA of claim 1, capable of expression in microorganisms or animal cells.
3. A DNA vector according to claim 2, which is plasmid pUC-118-p.GSPHx.
4. A transformant transformed with the vector of claim 2.
5. A transformant according to claim 4 which is a microorganism or an animal cell.
6. The transformant of claim 5, said microorganism being selected from the group consisting of *Escherichia coli, Bacillus subtilis* and *Saccharomyces cerevisiae.*
7. The transformant of claim 5, said animal cell being selected from the group consisting of monkey kidney cells and Chinese hamster ovary cells.
8. The transformant of claim 5, said animal cell being Chinese hamster ovary cells transformed with a virus vector containing an SV40 virus promoter.
9. The DNA vector of claim 2, which is a plasmid.

10. The plasmid of claim 9, said plasmid being prepared by inserting the DNA sequence of SEQ ID NO:1 into a starting plasmid selected from the group consisting of pUC118, pBR322, pBR325, pACYC184, pUC12, pUC18, pUC19, pUB110, pC194, pINI, pINIII, pTUB218, pTUB285, pAM82, pSVL and pSV2-dhfr.

11. A process for producing a glutathione peroxidase which comprises:
   culturing the transformant of claim 4 in a medium containing selenium to express the genetic information of said DNA, and
   collecting said glutathione peroxidase from the culture broth.

* * * * *